United States Patent [19]

Weiss et al.

[11] Patent Number: 4,563,427

[45] Date of Patent: Jan. 7, 1986

[54] CORROSION TEST ASSEMBLY

[76] Inventors: Mark D. Weiss, 1033 Brice Rd., Rockville, Md. 20852; Stephen W. Christoffersen, 6825 Kincaid Ave., Falls Church, Va. 22042

[21] Appl. No.: 546,597

[22] Filed: Oct. 28, 1983

[51] Int. Cl.$^4$ .................. G01N 31/00; G01N 17/00
[52] U.S. Cl. ........................................ 436/6; 422/53
[58] Field of Search .............. 422/53; 73/86; 110/184; 436/6; 203/1, 7

[56] References Cited

U.S. PATENT DOCUMENTS

| | | | |
|---|---|---|---|
| 3,174,332 | 3/1965 | Echtler, Jr. et al. | 73/86 |
| 3,197,698 | 7/1965 | Schaschl et al. | 73/86 X |
| 3,622,274 | 11/1971 | Richardson et al. | 73/86 X |
| 3,627,493 | 12/1971 | Manley | 73/86 X |
| 3,861,876 | 1/1975 | Robertson et al. | 73/86 X |

Primary Examiner—Barry S. Richman
Assistant Examiner—Lynn M. Kummert
Attorney, Agent, or Firm—E. Barron Batchelder

[57] ABSTRACT

A corrosion test assembly adapted for operative placement in a flowing gaseous medium for subjection to corrosive materials therein, more particularly, in scrubber systems, the assembly including a support and mounting means removably attachable to an outer surface of a component containing a flowing gaseous medium wherein at least one corrosion test specimen or coupon is mounted on the support and mounting means, with the test member extendable into the gaseous medium, wherein the test specimen is subjected to corrosive action by corrosive materials in the gaseous medium.

9 Claims, 10 Drawing Figures

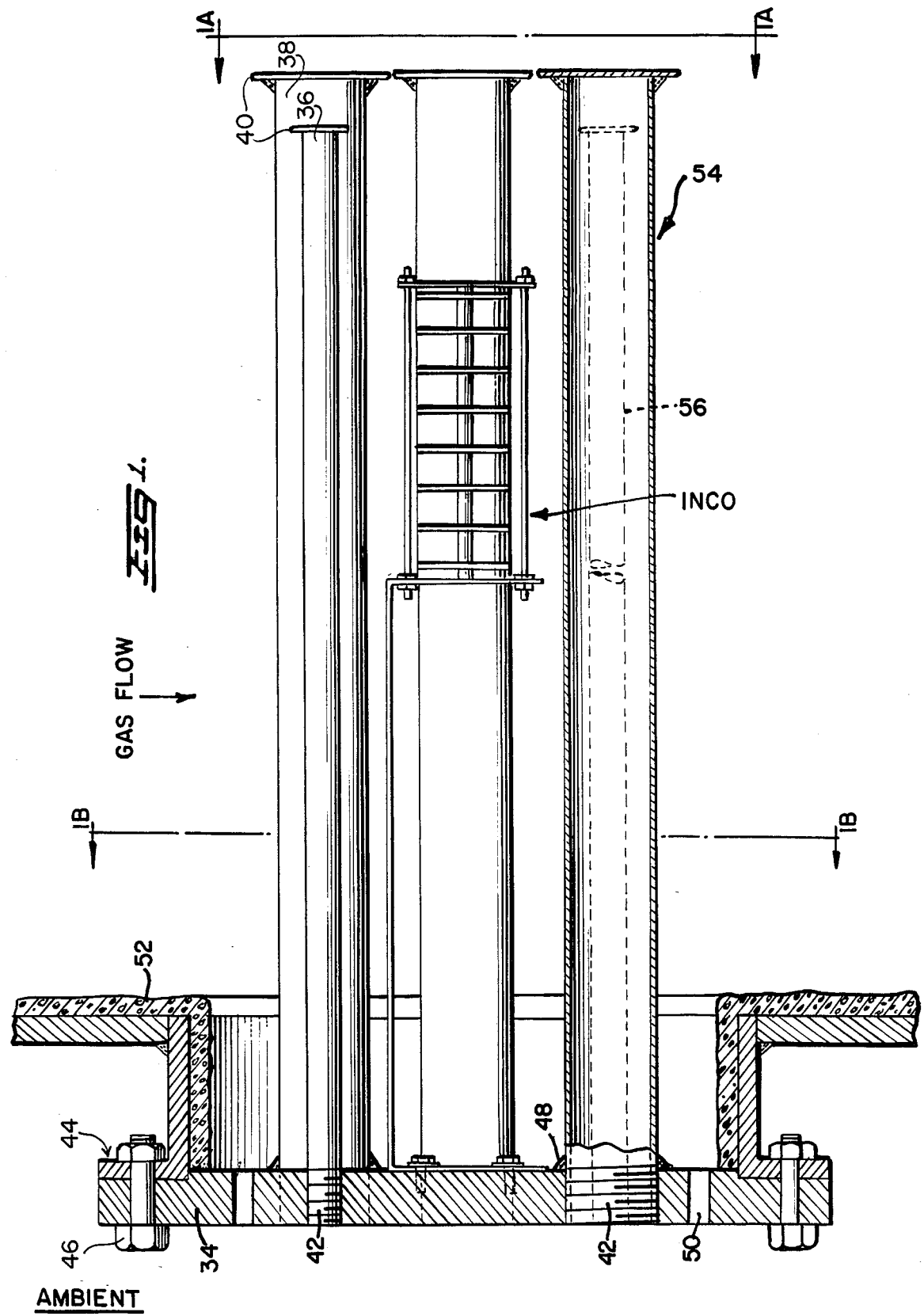

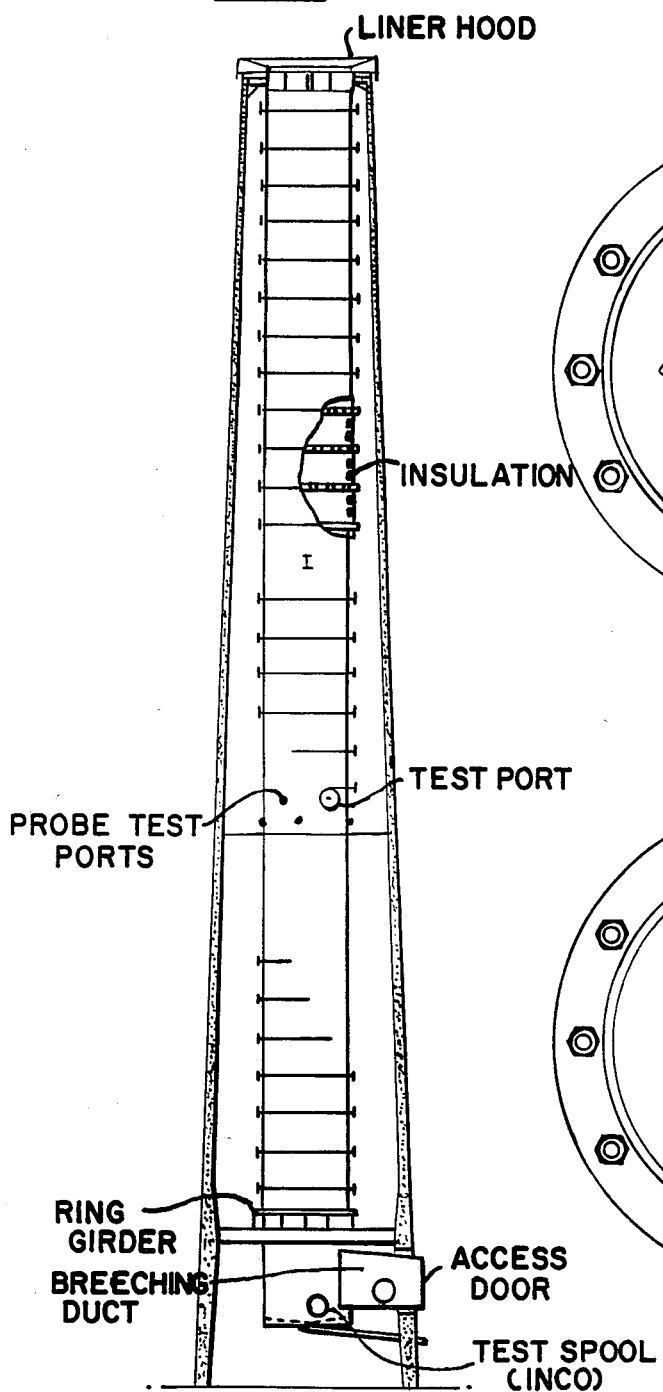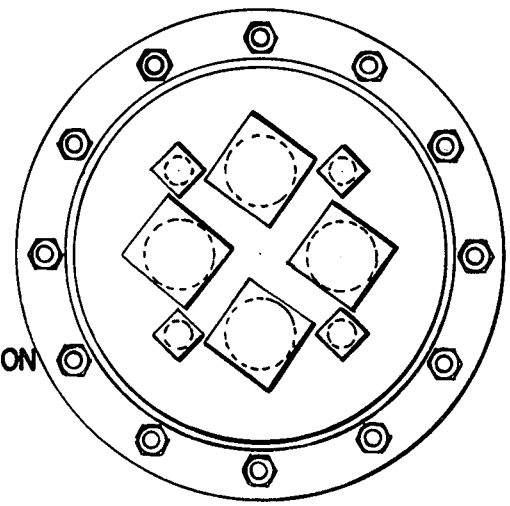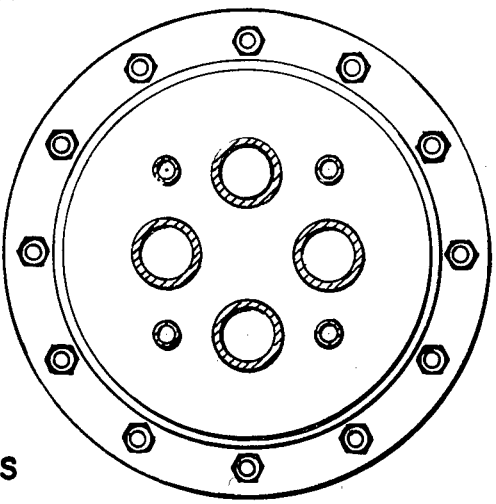

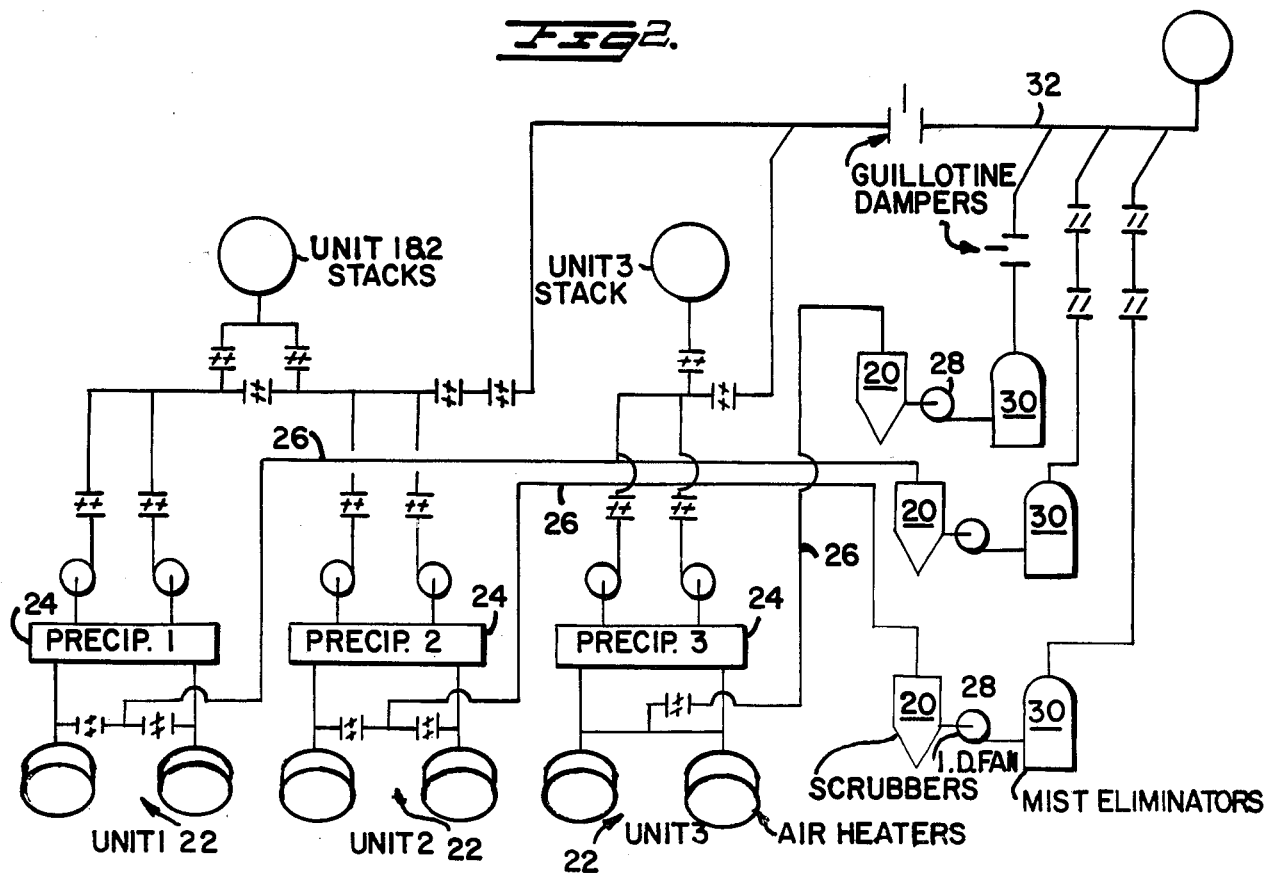
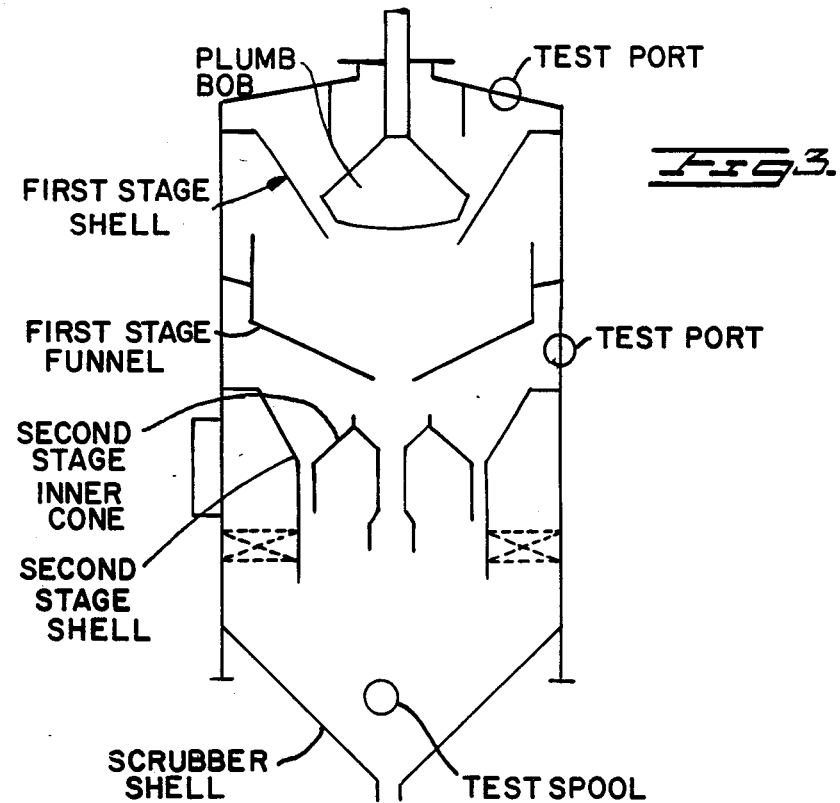

CORROSION TEST ASSEMBLY

FIELD OF THE INVENTION

The invention broadly relates to equipment or means to test corrosion factors in equipment designed to control air quality emissions, particularly to test corrosion in scrubbers associated with electrical generating processes or apparatus. The test device or assembly can be placed in different areas of a scrubber system and will serve, upon appropriate test procedures of individual test units or coupons, to yield information useful to an electric power generating facility and, more specifically, will yield information useful to the utility in choosing materials, such as linings, in the generating units.

With the recent addition of scrubbing systems to power plants, a variety of costly materials problems have evolved. In order to maintain or increase reliability of scrubber systems and to lower expensive replacement costs of components or portions of the system, various types of test units have been devised for testing corrosive action of the gases evolved in electric power generation.

Corrosion problems have plagued the scrubber industry for a lengthy period of time.

In approaching corrosion problems in the scrubber industry, various attempts have been made to determine corrosion factors as applied to different materials and even though components are selected to reduce corrosion, it is known that there are certain unknowns in surrounding environment and quirks in material behavior which increases the problems faced in attempting to utilize the most appropriate construction and materials in scrubbers.

BACKGROUND OF THE INVENTION

While corrosion problems have plagued the scrubber industry for years, with the recent addition of scrubbing systems to power plants, a variety of costly materials problems have evolved. Little information is available concerning the actual performance of materials incorporated into the various parts of complex scrubbing systems. In order to maintain or increase system reliability and lower component replacement costs, research programs have been initiated by various utilities and general testing facilities.

Information in the scrubber industry is in a general state of flux and is not readily transferrable from one system to another. Little information is available concerning the actual performance of materials incorporated into the various parts of the complex scrubber systems. Additionally, the atmosphere is generally corrosive, with such elements as chloride attacking scrubber components in a highly localized manner, e.g., in welds or crevices. While testing has been generally conducted to attempt to determine anticipated materials performance, the results in practice have often varied from what was expected. In large measure, this is probably due to multiple and often unknown variables within a scrubber system.

A further problem is involved in testing of materials in view of a peculiarity in many of electric generating plants, generally in that corrosion in the generating system usually takes places by pitting of materials and the corrosion is variable from one position to another in the system. Specific materials also are subjected to corrosion at different rates depending upon location in the system.

Heretofore, different types of testing devices have been used, such as, for example, electric resistance testing devices and test coupons, adapted for positionment in different areas or regions of a generating and scrubbing system. Neither of these devices are entirely suitable for measuring what appears to be the primary problem in scrubbers, i.e., pitting, as opposed to general corrosion. This is due to the fact that with pitting, there may be no loss of specific cross sectional area which could result in changes in evaluation of electrical resistance. In order to obviate this drawback, it appears that the only reliable means to evaluate pitting involves both visual inspection and a laboratory analysis of affected materials.

THE PRESENT INVENTION

The present invention is designed to more closely simulate actual construction methods encountered in scrubbers as distinguished from commercially available test coupons. Heretofore, there has not been an entirely satisfactory system or method of determining corrosion occurring in scrubber systems as specifically applied to electrical generating systems.

Generally speaking, the corrosion test assembly of the invention is constituted as a passive device designed to simulate scrubber conditions for the purpose of evaluating the resistance of materials and coatings to corrosive attack as they are exposed to variable and unknown conditions, while providing a means for testing for relative corrosivity due to heat differentials and which will not hinder the routine operation of the system. It obviously is not desirable to shut down operation of the system in order to observe and/or remove test materials for evaluation.

There are commercially available coupons which, in operation, give crevice, flat surface, cold work, and edge testing capability, plus optional weld bead. One of these is known as an INCO test spool manufactured by International Nickel Co. Additional devices can consist merely of a piece or plate of a material adapted for insertion in a scrubbing system or other location but these generally require a shut down of the system for removal for testing and otherwise do not provide all of the test results desired.

The present invention utilizes individual test devices or coupons which serve for testing, "as built" construction, including welding and ground surfaces. Of even greater significance, we have found that the present device is designed and serves to conduct heat away from the test specimen or coupon and an open end wall mount design provides access to ambient temperatures.

It is of further significance to note that the present invention can be readily affixed in any designed area of a component or system where it is desired to determine factors of corrosion of different materials to predict length of service and, therefore, to provide selectivity of materials for placement in these different areas.

The installation of these test assemblies, and the removal from, a component or system can take place without shutting down of the system. The overall corrosion test assembly can include a plurality of specifically different test units or coupons so that a most appropriate alloy metal or coated metal can be predicted for use in a given area dependent upon the test results.

Other objects and advantages of the present invention will become readily apparent to those skilled in the art from the following detailed description, wherein there is shown and described a preferred embodiment of the invention, simply by way of illustration of a currently preferred and contemplated mode for carrying out the invention. As will be realized, the invention is susceptible to other and specific embodiments, and materials, and details are capable of modification in various, obvious respects, all without departing from the invention. Accordingly, the drawings and description are to be regarded merely as illustrative in nature, and not as restrictive.

BRIEF DESCRIPTION OF THE DRAWINGS

FIG. 1 is an elevational view, partly in section and partly broken away, of a corrosion test assembly in accordance with the present invention and depicting various of the components thereof, as also means for mounting the test assembly in a desired location for conducting tests of corrosivity of different materials in a specific location in a system or component thereof;

FIG. 2 is a schematic gas flow diagram of an existing installation in an electric generating plant and depicting various components thereof schematically;

FIG. 3 is a schematic showing of a scrubber unit currently in use in the system of FIG. 2 and of a specified type as will be discussed hereinafter;

FIG. 4 is a sectional view of a 700-foot stack of the installation in the system of FIG. 2;

FIG. 1A is a top plan view of the corrosion test assembly of the invention taken generally along line 1A–1A of FIG. 1;

FIG. 1B is a sectional view taken along line 1B–1B of FIG. 1;

DESCRIPTION OF THE PREFERRED EMBODIMENT

Figure 5:
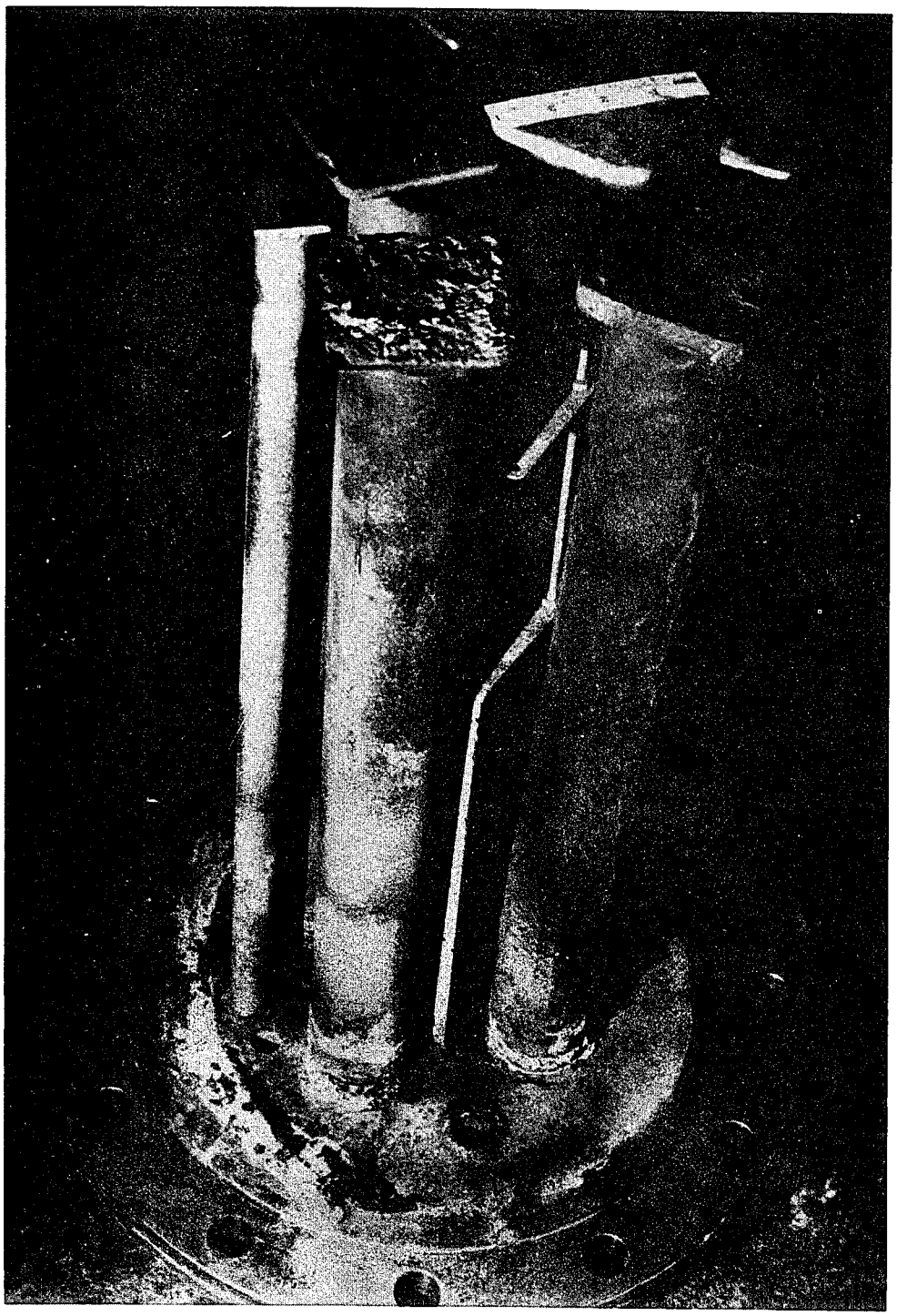
FIG. 5 is a perspective photographic reproduction of a test assembly after removal from service and testing installation disclosing some details of the effect of corrosion in different areas of the individual coupons or test specimens.
Figure 6:
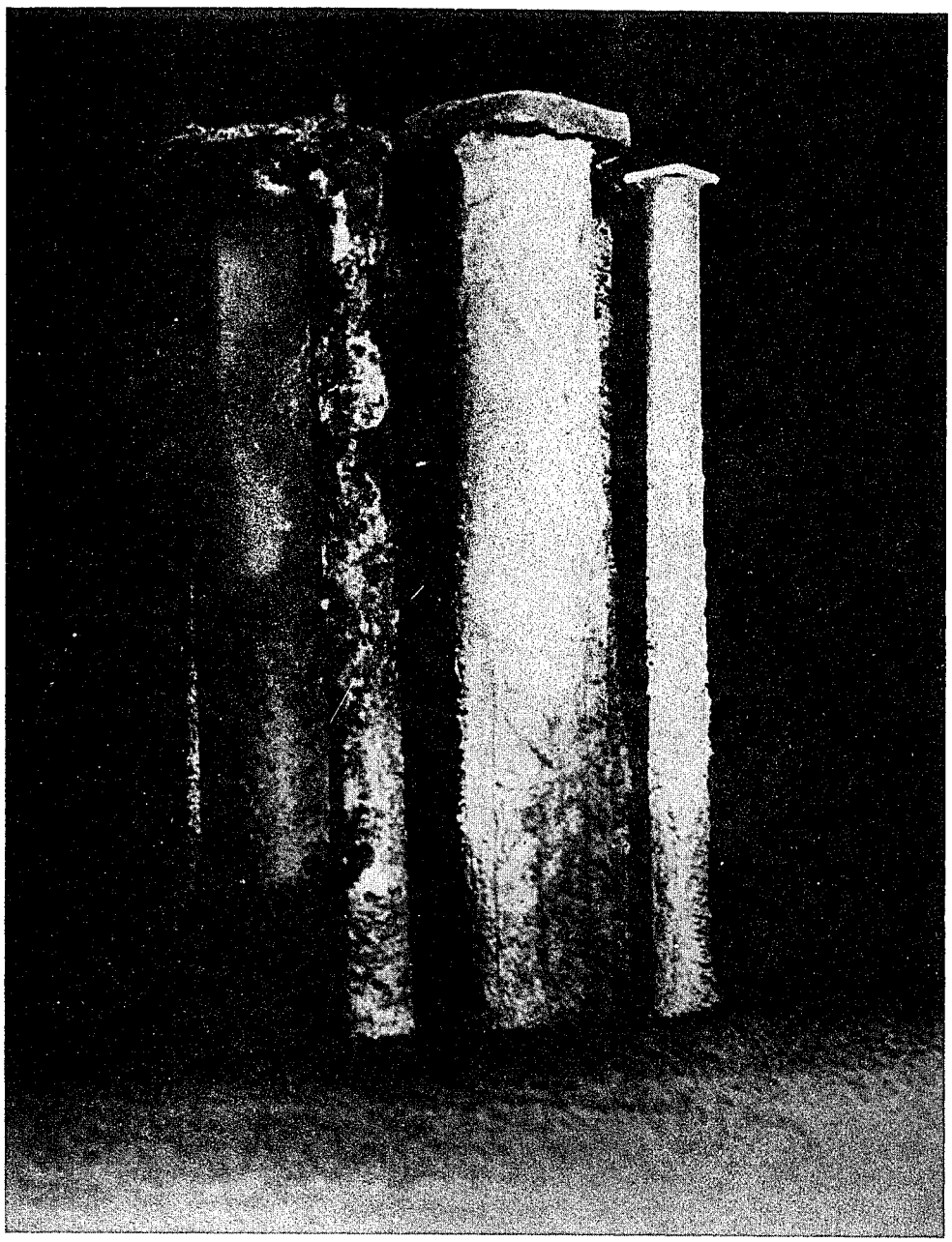
FIG. 6 is an elevational photographic reproduction view of a test assembly positioned at the location of turning vanes in a scrubber unit, and removed for test.
Figure 7:
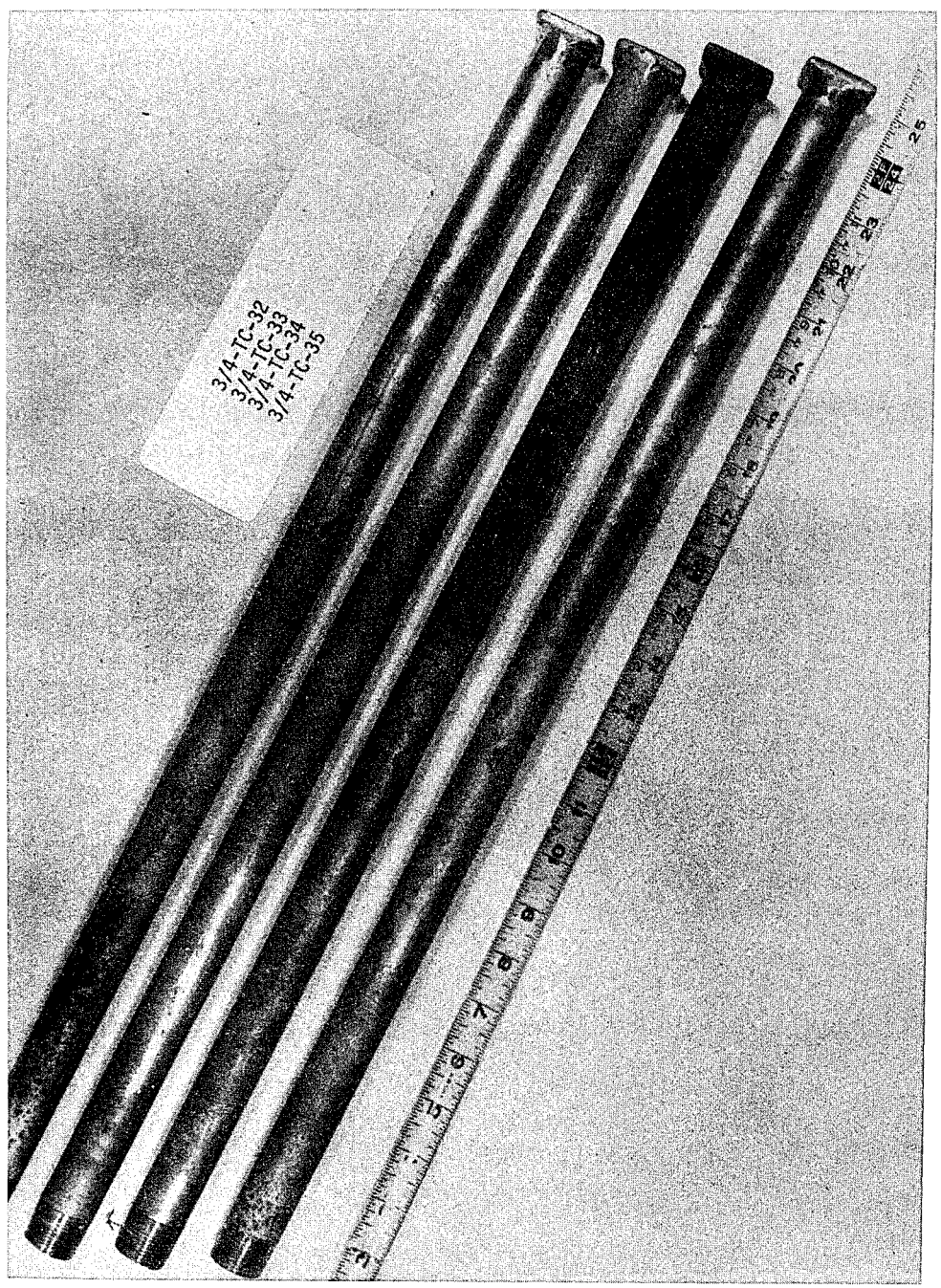
FIG. 7 is a reproduction of a photograph of individual test coupons or specimens consisting of Alloy G, subsequent to removal from the system and after being chemically cleaned by diluted hydrochloric acid showing corrosion.
Figure 8:
FIG. 8 is a reproduction of a photograph showing representative corrosion attack with large and deep pits scattered randomly along a length extending 8" beyond from the threaded end of the test coupon of a type shown in FIG. 7.

Broadly and summarily, the invention resides in a corrosion test assembly adapted for operative placement in a gaseous medium, such as in an electric power generating plant, for subjection to corrosive materials passing through the system. Containment means are provided in the system for the gaseous medium. An access opening is made in the containment means and a corrosion test assembly, including a support and mounting means, is selectively removably mountable or attachable on an outer surface of the containment means at the access opening. At least one corrosion test specimen or coupon is mounted on the support and mounting means and can consist of many different types of metals, alloys and coated or uncoated specimens. The overall test specimen extends through the access opening, with the support and mounting means operatively mounted or attached to the exterior, and with the test specimens or coupons extending into the gaseous medium in the component of the system wherein each test specimen or coupon is subjected to corrosive action of the corrosive material in the gaseous medium.

Referring now in detail to the drawings, even though the present invention is subject to modifications as above mentioned and as shown, it is principally adapted for use in scrubbing systems of or used in conjunction with electric generating systems of known types.

It is to be understood that the following description is directed to specific test specimens or coupons, and the results of corrosion attack for different materials placed in different locations in a scrubber system would deviate or be different one from another.

As will appear hereinafter, the concept of temperature differential has been found to be the key to testing as distinguished from traditional coupons which can be hung or mounted in various areas of the scrubber, but which do not simulate the "cold wall" effect which is of considerable importance to the integrity of materials. Temperature impacts materials and coating directly, as well as indirectly. Indirect effects involve condensation of corrosive elements in certain areas (increased corrosivity), as well as increasing the force for permeation, such as through coatings.

In order to more fully appreciate the scrubber system, a representative installation is depicted in the drawings. The system shown in FIG. 2 is for a generating station and is a depiction of the gas flow diagram. The system includes a plurality of scrubbers 20 which are of a Chemico-Venturi design with a removal of ash of approximately 99.5%. It is desirable to define the basic operation of such scrubbers to understand the problems involved. Flue gas exiting from each of the three 190 MW coal-fired boilers generally designated 22 is split in half. One flow enters electrostatic precipitators generally designated 24 while the other half passes, as shown by lines 26, through a particulate scrubbing system. The cleaned gases are then recombined before being discharged as noted in FIG. 2. Main material problems in this circuit occur in the components associated with the scrubbers; therefore, a closer scrutiny of this system is as follows. Gas enters from the top of the scrubber at 190° C. (245° F.). It is immediately quenched in the venturi to approximately 49° C. (120° F.) by a recycled slurry containing about 1–2% ash. This wet gas stream then passes through a throat and makes a 180° turn through a mist eliminator which removes a large percentage of the moisture and particulates. The gas makes another 180° turn and passes through a second venturi which is for future $SO_2$ removal capability (see FIG. 3). It then goes through a wet I.D. fan 28, a mist eliminator vessel 30, and exits through a single duct to a common header. At this point, the gas is recombined with an equivalent flow of hot gas from three precipitators. The final temperature of this mixture of gases is approximately 82° C. (180° F.). The gas stream then exits from the main header duct 32 out of a 213-meter (700-foot) stack (FIG. 4). The materials for the components in such a system are listed in Table #1.

TABLE 1

|  | Scrubber System #1 | Scrubber System #2 | Scrubber System #3 |
| --- | --- | --- | --- |
| Bull Nozzle | Carbon Steel | Carbon Steel | Carbon Steel |

TABLE 1-continued

|  | Scrubber System #1 | Scrubber System #2 | Scrubber System #3 |
| --- | --- | --- | --- |
| Scrubber Roof | Metalife 401 | Metalife 401 | Flakeglass |
| Scrubber Walls | Triflex Rubber | Triflex Rubber | Flakeglass |
| Venturi I.D. | Acid Resisting Brick | Acid Resisting Brick | 316 S.S. |
| Cheverons | PVC | PVC | PVC |
| I.D. Fan Inlet Damper | 316 S.S. | 316 S.S. | 316 S.S. |
| Fan Spray Pipe | 316 S.S. | 316 S.S. | 316 S.S. |
| Fan Impeller | Inco 625 | Inco 625 | Inco 625 |
| Fan Walls | Natural Rubber | Natural Rubber | Neoprene |
| Mist Eliminator Vessel | Triflex Rubber | Triflex Rubber | Flakeglass |
| Outlet Duct | Triflex Rubber | Triflex Rubber | Triflex Rubber |
| Outlet Damper | Incoloy 825 | Incoloy 825 | Hastalloy C-276 |

FIG. 3 schematically discloses a scrubber utilized in the system with the various components thereof designated, by name not numerals.

FIG. 4 discloses the 700-foot stack of the system as referred to above and the various components thereof are designated, also by name.

Referring to the materials, Table #1, it is interesting to note the variety, as well as the range, in corrosion resistant materials. For example, the gas inlet is fabricated from carbon steel and extends well into the scrubber vessel. This is due to the locally hot and relatively dry gas environment. The I.D. fans are of 316 stainless steel and it was found in operation that the inlet dampers were substantially corroded even though, only a few feet downstream, the spray nozzles were in relatively good condition. The latter is attributable to a constant flow of water on the pipes. In this system as used, it was found that the outlet damper No. 3, which was originally fabricated of Incoloy 825, was exhibiting profuse pitting. The bulk environment was thought to exist at a pH of 2.0 and containing chloride of 500 ppm. In examining corrosion data on Incoloy 825, the expected pitting rate would not appear to be severe. Evidently, the bulk environment differed from surface conditions. Following an ash deposit analysis, a replacement damper was fabricated from Hastalloy C-276 which remains in pristine condition after one and one-half years of service. Meanwhile, outlet dampers Nos. 1 and 2, made of Incoloy 825, which supposedly would be subjected to the same environment as damper No. 3 showed only varying degrees of moderate pitting following three and one-half years of service. Observing again Table #1, it is obvious that a multiplicity of coatings were used. As an example, the stack was lined with a vinyl ester which appears to have good chemical resistance although several anomalies occurred which were not explainable. This included such phenomena as spalling within the top 200 feet, cracking in areas of high vibration, and apparently a propensity of the coating to form long hairline cracks. It was also noted in the I.D. fans that two identical units having ¼" natural rubber linings on carbon steel lasted approximately three years before exhibiting blisters in need of major repairs. By the same token, one I.D. fan lined with ¼" neoprene, in the same environment, remained fine after approximately six years of service. The scrubber vessels themselves on units 1 and 2 are lined with a triflex natural rubber system, and unit No. 3 is a flakeglass system. It was found that with appropriate quality control, the flakeglass can perform very satisfactorily. Rubber, however, showed signs of degradation and, therefore, it was anticipated that shorter life than originally expected would take place. It is of substantial concern to the operators of the system how the materials perform, due to their direct bearing on the life of large capital items as well as the associated down times when repairing them. A large emphasis, accordingly, was placed upon studying the behavior of materials within the scrubber environment. It is this latter reason which led to the particular formation and construction of the corrosion test assembly of the invention. In the scrubbers as originally built, it was assumed that the materials of construction would provide a well defined, minimum life. Contrary to this, however, the life expectancy fell far short in several instances. During the problem occurrence, there was no clear course of action which could be taken and which would provide a full understanding for the failure of the various mechanisms. In light of the problems existing, a detailed study of the dynamics through the whole system was required. Such a formal materials test program was initiated and indirectly led to the present invention. A discovery program including literature was instituted and several various materials were noted including a coating system which appeared to be usable to increase various life lengths in the components of the given unit. Following this, a study including laboratory testing was instituted in order to be able to predict the behavior of, for example, stack coatings. Laboratory testing also was used to investigate coatings which would appear to be more suitable for the various components in the system as well as coatings which would appear to show promise as patching alternatives. Laboratory testing was also conducted on various alloys using condensate extracted from different areas within the system.

The laboratory testing, following the literature investigation then led to in situ testing. Initially, several Inco corrosion test spools were placed in several different locations in the scrubber, duct work and stack. These spools supply information on corrosion rates of alloys in different areas. Information obtained from these tests were then used for material selection of components which required replacement. To achieve a more sophisticated in situ testing program, alloy coupons were fabricated in a manner more representative of construction methods. An assembly of test units was devised which would represent several different aspects of fabrication and which could be inserted onto a test flange 34 in FIG. 1, FIG. 1A and FIG. 1B. The test units or individual components or coupons were designed basically to consist of a short length of pipe as shown at 36, 38 in FIG. 1. These pipe lengths were provided with a base plate 40 welded at one end, with the other end 42 being threaded. The pipes are fabricated from specified alloys and filler metals. Attention is invited to Table 2 which, across the top thereof, designates different materials well known in the metallurgical field. On the left hand of this Table, various of the components in the system are designated and to which the test specimens or coupons were attached, and measurements later taken which gave a true comparative value of the different materials for a given location in the system. Reference will be made later to this Table.

The corrosion test assembly of the invention has the pipes threaded onto the test flange. The flanges are mounted on nozzles 44 (FIG. 1) which can be retrofitted into the system so that various locations can be tested.

TABLE 2

| INCO vs COUPONS LOCATION | Duration (Days) | 316 Max Pit | 316 Max Rate | 317L Max Pit | 317L Max Rate | 904L Max Pit | 904L Max Rate | G Max Pit | G Max Rate | 825 Max Pit | 825 Max Rate | 625 Max Pit | 625 Max Rate | C4 Max Pit | C4 Max Rate | C276 Max Pit | C276 Max Rate |
|---|---|---|---|---|---|---|---|---|---|---|---|---|---|---|---|---|---|
| 1. Roof of Scrubber #3 | (B) | | | 30 | 50 | | | | | | | | | | | | |
|  | (A)219 | 48 | 82 | 27 | 46 | 30 | 51 | 40 | 68 | 47 | 80 | 7 | 12 | 4 | 7 | 0 | 0 |
| 2. Second stage Scrubber #3 | (B) | 45 | | | | 21$^9$ | 35 | 20 | | | | | 1 | | 1 | 2 | |
|  | (A)219 | 42 | 76* | 36 | 61 | 7 | 15* | 14 | 34* | 33 | 56 | 0 | 10* | 0 | 2* | 0 | 0 |
| 3. Scrubber #3 Turning Vanes | (B) | | | | | | | 78 | 130 | | | 1 | | | | 1 | 2 |
|  | (A)219 | 48 | 82 | 55 | 93 | 50 | 85 | 50 | 85 | 27 | 46 | 0 | 2* | 0 | 0.1 | 2 | 3 |
|  |  |  |  |  |  |  |  |  |  |  |  |  |  |  |  | 0 | 2* |
| 4. Common Header Duct - 1st Cross Bracing | 484 | 2 | 3 | 0 | 0.1* | 0 | 0.1* | 0 | 0.1* | 0 | 0.1* | 0 | 0 | 0 | 0 | 0 | 0 |
| 5. Common Header Duct - 2nd Cross Bracing | 484 | 1 | 2 | 0 | 0.1* | 0 | 0.1* | 0 | 0.1* | 1 | 2 | 0 | 0 | 0 | 0 | 0 | 0 |
| 6. Common Header Duct - 10th Cross Bracing | 484 | 5 | 7.6* | 14 | 11 | 9 | 7 | 27 | 20 | 0 | 4.9* | 1 | 2 | 0 | 0 | 0 | 0 |
| 7. Mounted Vertically on Stack Drain | 484 | 3 | 2 | 2 | 1.5 | 3 | 2 | 9 | 7 | 11 | 8 | 5 | 4 | 3 | 2 | 0 | 0.1* |
| 8. Mounted Horizontally on Stacked Door | (B) | | | | | | | 2 | | 3 | | | | | | 0 | 0 |
|  |  |  |  |  |  |  |  | 49 | 82 |  |  |  |  |  |  |  |  |
|  | (A)219 | 11 | 19 | 13 | 22 | 4 | 7 | 0 | 3.5* | 0 | 5* | 0 | 0 | 0 | 0.1* | 0 | 0.1* |
| 9. Stack Elevation 295' | (B) | | | 18 | | 113 perf. | <188 | 105 | 175 | 11 | 18 | 4 | | | | | |
|  | (A)219 | 17 | 29 | 15 | 30* | 25 | 43 | 32 | 55 | 13 | 22 | 1 | 7* | 0 | 0 | 0 | 0 |

MAX PIT: Maximum Pit Depth (Mils)
MAX Crevice Depth (Mils) Noted in upper right hand corner if greater than max pit depth
MAX RATE: Maximum pitting corrosion rate (Mils per year): *Crevice attack, *uniform attack, >pit attack By mounting the pipe samples on the flange, it is possible to insert and withdraw the corrosion test assemblies while the units are running and which is very desirable as above pointed out. The information obtained from the test spools as so manufactured and mounted were compared with previous known Inco spools and laboratory testing conducted. In Table 2, the numerals in the lines designated (A) refer to figures of the Inco spool while those in line (B) are for the various materials itemized at the top of the table. This table or matrix includes the corrosion data compiled from testing of the corrosion test assemblies and coupons thereon with the Inco test spools. Those boxes which contain both types of results are indicative of similar materials tested in the same location. It is to be noted that in substantially all instances, the corrosion coupons of the present invention exhibited a higher corrosion rate. This is especially true in the hotter regions of the system (the point where the 120° F. scrubber gas combines with the 245° F. precipitator gas, after location No. 3). It is believed that this phenomenon is due to cooler surface temperatures created by a large $\Delta T$ across the coupon thickness. It will also be apparent from the reproduced photographs that the corrosion is greater and the pitting deeper and more complex primarily near the threaded ends thereof, i.e., the coolest end. These photographs of actual test units are indicative or representative of the type of corrosion which can be expected if the designated alloys are used as a wall of the stack or header duct. Manifestly, other alloys and/or metals and coatings, follow testing and/or practical use, will be found to have more desirable characteristics and results.

It is to be noted that various of the pipe coupons attached to the test flanges can consist of carbon steel with a protective coating while others consist of alloys as shown in the tables. The coupons, as pointed out above, can, on their base, be inserted in and removed from the system while still in operation. They are attachable to the exterior of any of the components of the system, following a perforation of the component as and at a desired location, by means of the nozzle and the bolts 46 as shown in FIG. 1. Various coatings have and can be tested to obtain the best service results in a given location in a scrubber system or the like.

Because of its apparent great significance, it is again pointed out that the pipe coupons incorporate a factor which may be instrumental in determining corrosion behavior. This factor is a $\Delta T$ which is established across the wall thickness of the pipe. This differential is established by virtue of the threaded end which is opened to ambient conditions. For the alloy coupons, this provides a surface which will tend to condense the gas, much like a vessel wall would. The $\Delta T$ is also important in that it establishes a driving force which determines rate of permeation through a coating. The amount of temperature differential appears to be very significant in determining the life of the coating. The exact effect is still being researched and the end reasoning or result is not at this time known, although the results are. It is known that the $\Delta T$ between the gas side of the vinyl ester in the stack and insulated steel on the ambient side is 25° C. (45° F). In laboratory monitoring of vinyl ester, using a $\Delta T$ of 50° C. (90° F.) across the steel coating cross section some cracking of the coating occurred several days after removal from a testing solution. Furthermore, when using a $\Delta T$ of 105° F., profuse blistering was clearly evident on the coated surface in only a matter of several weeks. This information as correlated does provide a story of material behavior and life expectancy of a stack liner for example.

Localized conditions at a given surface must be determined and understood. Various temperature gradients should be measured which exist along a stack and main header duct and in the scrubber. Condensate can be withdrawn from these various points and can be utilized for further testing of the materials. It is also desirable to stay abreast on operational control of any system. It is also of great significance that frequent inspections be made. This includes interior surface conditions of components, and a study and laboratory and physical examination of the individual parts and components will serve to give a substantial improvement in conclusions of materials to be used and their anticipated results.

The corrosive results on the individual test pipes or coupons can readily be seen from the reproduced photographs and here it is to be noted again that the greatest pitting effect appears to be in the region of the threaded end of the pipes, i.e., where the cooler surfaces are provided by subjection to ambient temperatures as distinguished from external temperatures due to placement in the flow of heated gases. One point, for example, where hotter regions result in higher corrosion rates takes place at the point where a 120° F. scrubber gas combines with the 245° F. precipitator gas after location 3 as heretofore pointed out.

The close examination and follow-up of testing on the actual test assemblies results in better overall end results.

Attention is also invited, in the photographs, to the accumulation of fly ash on the samples, and disclosure of the sealant 48 used at the base of the pipe/flange connection, and the testing penetrations designated 50, respectively. The sealant can consist of a silicone sealer or Teflon tape and serves to galvanically insulate the pipe and the flange. The protective lining 52 (FIG. 1) serves to protect the duct wall and nozzle material. The holes or penetrations 50 are typical for environment monitoring, such as temperature, velocity, etc. It will also be seen in FIG. 1 that the ambient temperature area has been designated externally of the corrosion test assembly unit, and the gas flow is depicted by the arrow 2. It is also to be noted in FIG. 1 that coated pipes 54 of two-inch diameter are utilized in one assembly, and that four pipes 56 are of a one-inch diameter and consist of alloy materials.

Obviously, it can be seen, that there is no simple method for controlling material problems in scrubbing systems. Close cooperation is required from plant operators, plant engineers, office engineering, etc., in order to obtain low maintenance, and an efficient running operation. Materials engineering can likewise, with cooperation from all parties involved, help increase system reliability.

The foregoing description, when taken in conjunction with the drawings, disclose specifics of various items utilized in a corrosion test assembly and which is adapted to approximate in so far as possible the corrosion problems in different areas of a system, including a scrubber system, and the test coupons or test specimens reproduce, as closely as possible, conditions which will take place in an overall system. It is to be noted that the test specimens or coupons are mounted on a removable flange and the test assemblies on these flanges can be placed in different areas of the system and components thereof. Preferably each of the removable flanges has mounted thereto test specimens which can differ one from another. The coupons per se are comprised of a plate welded to a pipe. For those fabricated from alloys, corrosion rates in the weld, heat affected zone such as where the plates are welded to the free ends of the pipes, the edge of the plate, the plate surface, and the surface of the pipe might be different or vary due to microstructural variations. These differences must be considered when specifying construction materials for the scrubbers.

Coated coupons consist of carbon steel plate welded to a carbon steel pipe which is subsequently sand blasted and coated with chemically resistant paint. Such a coupon or test specimen not only allows evaluation of a coating's resistance to the environment but will simulate application limitations such as found over welds, rounded edges, and small diamter supports or pipe.

Some of the carbon steel test specimens are left uncoated in order to determine their anticipated life in a scrubber system or to be able to better study the resultant effect of passage of corrosive materials in the gas flow stream thereby.

Other advantages of the test specimens are due to the fact that they are simply threaded into place on the base or mounting member and the base or mounting member can be affixed over a penetration and the test specimen retrofitted into any portion or member of the system as desired. Upon removal of the test specimen and its mounting flange, cover plates can be utilized to close the penetrations.

The present invention accordingly is designed to more closely simulate actual construction methods encountered in the scrubber and system than are commercially available test coupons. As pointed out above, the present test specimen is a passive device designed to simulate in as many areas as possible conditions existing in scrubber systems, for the purpose of evaluating the resistance of materials and coatings to pitting or corrosion as they are exposed to variable and unknown conditions, while providing a means for testing for relative corrosivity due to heat differentials which occur by virtue of a $\Delta T$ which is established across the wall thickness of the pipe. This differential is established by virtue of the threaded end which is open to ambient conditions. For the alloy coupons this provides a surface which will tend to condense the gas, much like a vessel wall would in operation. The $\Delta T$ is also important in that it establishes a driving force which determines the rate of permeation through a coating, it being understood that all coatings used in such a system are permeable and the present structure provides a true test of resistance to corrosion or permeation of a coating.

In essence therefore the present invention is designed to simulate scrubber conditions for the purpose of evaluating the resistance of materials and coatings to pitting as they are exposed to variable and unknown conditions, while providing a means for testing for relative corrosivity due to heat differentials, which will not hinder the routine operation of the system. The importance of this latter concept, i.e., continued operation, is obvious in that the overall system need not be turned off or deactivated.

While commercially available coupons, such as the referred to Inco device give crevice, flat surface, cold work, and edge testing capability plus optional weld bead, the present invention adds the factors of graining, "as built" construction, including welding and ground surfaces. Most importantly, however, the device is designed to conduct heat away from the test specimen, and the open end wall mount design provides access to ambient temperatures. It is believed that the concept of temperature differential is a key to the testing. While traditional known coupons can be hung or mounted in various areas of the scrubber, they do not simulate the "cold wall" effect which is of considerable importance to the integrity of materials. Temperature impacts materials and coating directly, as well as indirectly. Indirect effects involve condensation of the exterior of coated elements or test units in certain areas, cause increased corrosivity, as well as increasing a force for permeation through the coatings in the nature of a driving force. This temperature differential is representative of actual service conditions of a vessel wall, such as the exterior or top walls or surfaces of a scrubber per se. The ΔT is significant in the coated coupon in that it establishes this driving force of the corrosive media to the steel substrate. In the case of the alloy, the ΔT may establish a condensing surface on the environment (gas) side, thus representing a vessel wall behavior.

In order to provide access to the test specimens at any time as well as a mounting location, test flanges were designed and to hold four alloy coupons, four coated coupons, one alloy test spool such as an Inco spool supplied by an alloy manufacturer, and further test ports are provided for temperature and condensate monitoring.

The present invention accordingly provides the closest known approach to actual conditions which might exist in an electric power generating plant including a scrubber system, the latter becoming more significant to protect surrounding environment.

While a specific device and construction has been shown in the drawings, minor variations therein will be obvious to those skilled in the art without departing from the spirit of the invention. Such obvious changes or modifications are considered to be within the scope of the inventive concept as expressed herein, and as claimed hereinafter.

What is claimed is:

1. A method of determining corrosive effects on components within a gas scrubber system, said method comprising mounting a plurality of test specimens on a removable mounting means, on the exterior of a component of a scrubber system, with said test specimens extending into the interior of said component, each said corrosion test specimens being constituted of a pipe section having a first end thereof threaded for mounting in a coactive threaded opening in the support means and a second interior end of each pipe section being closed by a test coupon, exposing the threaded end of the pipe sections to the environment exterior to the location in which a scrubber system component is placed, the interior of the pipe sections thereby being open to the exterior environment and the exterior surface of the pipe sections within the component being heated by gas flow passing thereby, wherein the respective internal and external temperatures of the pipe sections create a cold wall effect and a condensing surface on the exterior of the pipe sections and a driving corrosive force through a coating which is on the exterior of at least one of said pipe sections.

2. An in situ corrosion test assembly adapted for operative placement in a flowing hot gaseous medium for subjection of components of said test assembly to corrosive materials in said medium, said assembly comprising a means for containing a flowing hot gaseous medium including an access opening therein, a test specimen support and assembly mounting means removably attachable on an outer surface of said containment means at said access opening, at least one corrosion test specimen mounted on said test specimen support and mounting means, each said test specimen consisting of a hollow pipe, a first end thereof being closed, said at least one test specimen positioned with said closed first end extending through said access opening into said containment means when said support and mounting means is in an operative mounted position on said containment means, so as to extend into the hot flowing gaseous medium therein with the exterior surface of said test specimen subjected to a corrosive action by corrosive materials in the gaseous medium, said hollow pipe having a second open end, said open end being exposed to the environment external to said containment means, the external and internal walls of said pipe thereby being exposed to different heats of contacting media, and thereby creating a cold wall effect on the external pipe wall, tending to condense moisture in said flowing gaseous medium into an corrosive liquid from constituents in the medium which coacts with the material of the pipe thereby causing corrosive external pitting thereof.

3. An in situ corrosion test assembly adapted for operative placement in a flowing gaseous medium for subjection to corrosive materials therein, the assembly comprising a component means for placement in a scrubber system containing a flowing hot gaseous medium, said component means having a test port opening therein, a test specimen support and mounting means removably attachable to an outer surface of said component means at said test opening thereof, at least one corrosion test specimen mounted on said support and mounting means, said support and mounting means having an opening therethrough, each said test specimen consisting of a pipe having a first end and a second open end which is adapted for connection with the opening in said support and mounting means, wherein the first end of each said corrosion test specimen extends through said test opening within said scrubber system component, means when the assembly is attached thereto said first end of said test specimen being closed by a flat plate welded over said first end, the open second end of said pipe and the interior of said pipe being open to the environment external to the scrubber system component means the interior and exterior of the pipe being subjected to a heat differential due to disposition of the exterior of the pipe within a corrosive environment and the second open end thereof being open to the environment external to the component means, said heat differential causing in effect a cold wall or condensing external surface on the pipe and a driving corrosive force from the exterior toward the interior of said pipe.

4. A corrosion test assembly as claimed in claim 3 and including a plurality of said test specimens mounted on said support and mounting means, each of said test specimens constituting an open pipe with a threaded second end engaged in a threaded opening in said support and mounting means for exposure of the interior of the pipe to the external surrounding environment of the scrubber system component means, each pipe having a plate welded on and over the first pipe end whereby the plate material and welding material are subjected to corrosive action of corrosive materials in the flowing gaseous medium and simulating junctures and connections of said component of a scrubber system, the entire exterior surface of each of said test specimen pipes within the scrubber system component means being subjected to corrosive action.

5. A corrosion test assembly as claimed in claim 4, wherein some of said test specimens are composed of metal alloys and other of said specimens are composed of unalloyed metal material and further wherein at least one test specimen has a protective coating material applied to the exterior thereof.

6. A corrosion test assembly as claimed in claim 5 wherein each of said test specimens comprises a different exterior surface material exposed to said corrosive environment.

7. A corrosion test assembly as claimed in claim 6, wherein at least one of said test specimens is a coated carbon steel pipe and the driving corrosive force due to the cold wall effect causes a permeation through the coating on said carbon steel pipe thereby enabling testing of the resistivity and permeability of said coating to said corrosive environment.

8. A corrosion test assembly as claimed in claim 7, wherein the support and mounting means pipes includes means defining openings therethrough adjacent to the test specimens and being adapted for insertion of test means therethrough and into the gas stream within the scrubber system component.

9. A corrosion test assembly as claimed in claim 7, wherein one of said pipes is constituted of uncoated carbon steel for comparison purposes with the remainder of said coated carbon steel pipes.

* * * * *